United States Patent
Chang et al.

(10) Patent No.: US 6,214,328 B1
(45) Date of Patent: Apr. 10, 2001

(54) STIFF-FEEL HAIR STYLING COMPOSITIONS

(75) Inventors: Ching-Jen Chang, Ambler; Andrea Claudette Keenan, Plymouth Meeting; Curtis Schwartz, Ambler, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/391,561

(22) Filed: Sep. 8, 1999

Related U.S. Application Data

(60) Provisional application No. 60/099,897, filed on Sep. 11, 1998.

(51) Int. Cl.$^7$ ................................................. A61K 7/11
(52) U.S. Cl. ..................... 424/70.16; 424/70.11; 424/47
(58) Field of Search ........................ 424/70.1, 70.11, 424/70.16, 47

(56) References Cited

U.S. PATENT DOCUMENTS

| 4,196,190 | | 4/1980 | Gehman et al. . |
| 4,859,455 | * | 8/1989 | Nowak, Jr. et al. . |
| 5,100,658 | * | 3/1992 | Bolich, Jr. et al. . |
| 5,658,558 | | 8/1997 | Schwartz . |

FOREIGN PATENT DOCUMENTS

| 761119 | 3/1997 | (EP) . |
| 4-59719 | 2/1992 | (JP) . |

* cited by examiner

*Primary Examiner*—Thurman K. Page
*Assistant Examiner*—P. E. McQueeney
(74) *Attorney, Agent, or Firm*—Thomas J. Howell

(57) ABSTRACT

A method for enhancing the performance of hair fixative resins in hair styling compositions by using selected polymers having certain compositions is disclosed. In particular, the present invention involves a method of improving the stiffness performance of hair fixative resins by using polymers containing 5–95% ($C_1$–$C_{10}$)alkyl (meth)acrylate, 0–70% hydroxyalkyl (meth)acrylate, 0–50% monocarboxylic acid monomer and 1–25% dicarboxylic acid monomer. The selected polymers are particularly useful in aqueous hair styling compositions containing low (80% or less) volatile organic compound (VOC) concentrations.

18 Claims, No Drawings

STIFF-FEEL HAIR STYLING COMPOSITIONS

This is a nonprovisional application of prior pending provisional application Ser. No. 60/099,897 filed Sep. 11, 1998.

BACKGROUND

The present invention relates to hair styling compositions and a method of enhancing the performance of hair fixative resins. More particularly, the present invention relates to a method of improving the stiffness performance of hair fixative resins. In a preferred embodiment, the present invention also relates to aqueous hair styling compositions containing low (80 weight percent or less) volatile organic compound (VOC) concentrations.

Hair styling products, such as hair sprays, styling gels, spray gels and mousses are used on hair to hold the hair in a particular shape or configuration. The hair styling products, when applied, form a thin film or weld of resin on the hair, most efficiently in the seam between adjacent hair fibers or at a point where the fibers cross one another, and, as a result, hold the hair in a particular shape or configuration.

Hair styling products can be applied to the hair in several ways. For example, the hair styling product may be applied by a spray using a propellant (such as in an aerosol hair styling product), using a hand pump, or, in the case of a gel, applied to the hair by hand directly. Hair styling products typically contain one or more VOC. VOC contribute to ground level air pollution in the presence of sunlight and air, and are volatile under ambient conditions.

Legislation in New York, California and other states mandates that the amount of VOC formulated into hair styling products that are sprayed, such as aerosol and pump hair sprays, must not exceed 80 weight percent (%) in the product. By June 1999, the amount of VOC in hair styling products that are sprayed must be reduced to 55% in California. Other states have enacted similar legislation mandating the reduction of VOC in hair styling products that are sprayed. Present hair styling products in the United States that are sprayed typically have VOC levels of 80% or less. Such VOC include, for example, ethanol, dimethyl ether and hydrocarbons; the most likely replacement for VOC is water.

In order for a resin to be suitable in a hair spray composition it must exhibit a combination of desirable performance attributes. These include, but are not limited to, compatibility of the resin in the hair spray composition, satisfactory high humidity curl retention, satisfactory stiffness on the hair, low tackiness after spraying on the hair, short dry times, no visible residue on the hair, easy shampoo removability, and easy sprayability resulting in a uniform mist of spray delivered to the hair.

Hair fixative resins available in the marketplace today, for example, Amphomer LV-71 (octylacrylamide/acrylates/butylaminoethyl methacrylate copolymer) and Resyn 28-2930 (vinylacetate/crotonic acid/vinylneodecanoate copolymer) satisfy many of these performance attributes, but only in hair spray compositions containing a limited amount of formulated water, for example, less than 15%, such as usually found in 80% VOC hair spray compositions (Amphomer and Resyn are trademarks of the National Starch and Chemical Company). These resins are compatible in the hair spray composition, and give a firm, stiff feel to the hair, but are deficient in either residue properties or curl retention. In particular, these resins are unsuitable in 55% VOC hair spray compositions (containing significant amounts of formulated water) due to poor spray properties from high viscosity, incompatibility in the hair spray composition, or having extended dry times.

U.S. Pat. No. 4,196,190 discloses acrylic hair fixative resins containing 10–30% of an alkyl acrylate, 41–60% of methyl methacrylate, 5–20% of hydroxyethyl methaerylate and 10–30% of methacrylic acid. Although disclosing acrylic hair fixative resins that are compatible in 55% VOC hair spray compositions containing large amounts of formulated water, give excellent high humidity curl retention, excellent shampoo removability, short dry times, low or no tackiness, but deliver a soft, natural feel to the hair, this reference does not disclose or suggest how to improve the stiffness of the resin on the hair. Although a soft feel to the hair is desirable for those formulators targeting a more manageable, natural feeling hair style, a significant portion of the population prefers a stiff, firm hold to the hair.

U.S. Pat. No. 5,658,558, although disclosing how to improve the performance of acrylic resins in low-VOC systems, also does not disclose how to improve hair stiffness.

The present invention seeks to improve upon the prior art hair fixative resin technology by using selected polymers as hair fixative resins that are compatible in hair fixative compositions containing large amounts of water, for example, 55% VOC compositions, while retaining other beneficial hair fixative properties, such as (i) low tackiness, (ii) short dry times, (iii) easy shampoo removability, (iv) excellent high humidity curl retention, (v) easy sprayability, and in addition, delivering a stiff, firm hold to the hair, rather than a soft feel to the hair.

STATEMENT OF INVENTION

One embodiment of the present invention provides an aqueous hair styling composition comprising (a) from 1 to 15 weight percent of at least one acrylic hair fixative resin, wherein the acrylic hair fixative resin is a polymer comprising as polymerized units: (i) 5 to 95 weight percent of at least one $(C_1-C_{10})$alkyl (meth)acrylate, (ii) from zero to 70 weight percent of least one hydroxyalkyl (meth)acrylate, (iii) from zero to 50 weight percent from of at least one $C_3-C_8$ monoethylenically unsaturated monocarboxylic acid monomer and (iv) from 1 to 25 weight percent of at least one $C_4-C_8$ monoethylenically unsaturated dicarboxylic acid monomer, based on total weight of the acrylic hair fixative resin; and (b) at least one neutralizer.

In another embodiment the present invention provides the aforementioned aqueous hair styling composition further comprising volatile organic compounds in a concentration up to 98 weight percent, based on total weight of the aqueous hair styling composition.

In a preferred embodiment the present invention provides aqueous hair styling compositions using the aforementioned hair fixative resins wherein (a) the $(C_1-C_{10})$alkyl (meth)acrylate is from 2 to 67 weight percent of at least one $(C_2-C_5)$alkyl acrylate and from 5 to 71 weight percent of methyl methacrylate, (b) the hydroxyalkyl (meth)acrylate is from 2 to 26 weight percent of hydroxyethyl methacrylate, (c) the $C_3-C_8$ monoethylenically unsaturated monocarboxylic acid monomer is from 2 to 30 weight percent of methacrylic acid, and (d) the $C_4-C_8$ monoethylenically unsaturated dicarboxylic acid monomer is from 2 to 10 weight percent of itaconic acid.

The present invention further provides a method for increasing the stiffness on hair of aqueous hair styling compositions comprising introducing from 1 to 15 weight percent of an acrylic hair fixative resin, based on total weight of the aqueous hair styling composition, into a hair styling composition, wherein (a) the acrylic hair fixative resin is a polymer comprising as polymerized units: (i) 5 to 95 weight percent of at least one $(C_1–C_{10})$alkyl (meth)acrylate, (ii) from zero to 70 weight percent of least one hydroxyalkyl (meth)acrylate, (iii) from zero to 50 weight percent from of at least one $C_3–C_8$ monoethylenically unsaturated monocarboxylic acid monomer, and (iv) from 1 to 25 weight percent of at least one $C_4–C_8$ monoethylenically unsaturated dicarboxylic acid monomer, based on total weight of the acrylic hair fixative resin; and (b) the hair styling composition comprises at least one neutralizer.

DETAILED DESCRIPTION

The aqueous hair styling compositions of the present invention provide enhanced stiffness performance of the hair styling composition. We have found that the use of certain selected acrylic polymers surprisingly improves the stiffness on hair of the hair styling composition without adversely affecting other properties of the hair styling composition.

By an "aqueous hair styling composition" we mean a hair spray, styling gel, spray gel or mousse that is used on hair to hold the hair in a particular shape or configuration. Preferably, the hair styling composition in the present invention is a hair spray.

By "hair" we mean natural human hair, animal hair, artificial hair and wigs or hairpieces comprising hair.

As used herein, all percentages referred to will be expressed in weight percent (%) unless specified otherwise.

The aqueous hair styling compositions typically will contain at least 2% and up to 98% water, more typically, from 25 to 70% water, based on the total weight of the aqueous hair styling composition. By "low-VOC" we mean the hair styling composition contains 80% or less volatile organic compounds, that is, usually about 10% or more of water. Preferably, the hair styling composition contains less than 70%, and more preferably 55% or less, VOC. Optionally, the hair styling composition may contain no VOC.

The term "(meth)acrylate" means methacrylate or acrylate. The term "(meth)acrylic acid" means methacrylic acid or acrylic acid. As used herein, the term "unsaturated dicarboxylic acid monomer" refers to monoethylenically unsaturated dicarboxylic acids containing 4 to 8, preferably from 4 to 6, carbon atoms per molecule and anhydrides of the corresponding dicarboxylic acids. Dicarboxylic acid monomers useful in the water-soluble polymers of the present invention include, for example, maleic acid, maleic anhydride, fumaric acid, α-methylene glutaric acid, itaconic acid, itaconic anhydride, citraconic acid, mesaconic acid, cyclohexenedicarboxylic acid, and water-soluble salts thereof When the word "soluble" is used to further describe a compound, such as for example the "soluble hair fixative resins," we mean herein that the compound described is soluble in the low-VOC hair styling composition.

As used herein, VOC are compounds containing at least one carbon atom and are typically used as solvents or propellants in hair styling compositions. VOC include, for example, $C_1–C_{12}$ straight or branched chain alcohols such as methanol, ethanol, propanol, isopropanol and butanol; $C_1–C_{12}$ straight or branched chain hydrocarbons such as methane, ethane, propane, isopropane, isobutane, pentane, isopentane and butane; or ethers such as dimethyl ether and dimethoxymethane. Preferred VOC are selected from one or more of ethanol, isopropanol, n-propanol, dimethoxymethane, dimethylether and $C_1–C_{12}$ straight or branched chain hydrocarbons.

The acrylic hair fixative resins useful in the present invention are soluble in the low-VOC hair styling composition "as is" or upon neutralization of some or all of the acid groups contained in the acrylic hair fixative resins.

The acrylic hair fixative resins of the present invention comprise as polymerized units (1) from 5 to 95%, preferably from 45 to 90%, and more preferably from 70 to 80% of at least one $C_1–C_{10}$ straight or branched chain alkyl (meth) acrylate monomer, (2) from zero to 70%, preferably from 2 to 26%, and more preferably from 5 to 20% of at least one hydroxyalkyl (meth)acrylate monomer, (3) from zero to 50%, preferably from 2 to 30%, and more preferably from 12 to 26% of at least one $C_3–C_8$ monoethylenically unsaturated monocarboxylic acid monomer, and (4) from 1 to 25%, preferably 2 to 10, and more preferably from 3 to 8%, of at least one $C_4–C_8$ monoethylenically unsaturated dicarboxylic acid monomer based on the total monomer used to form the acrylic hair fixative resin.

Preferably, the $(C_1–C_{10})$alkyl (meth)acrylate is selected from one or more $(C_1–C_5)$alkyl (meth)acrylates such as, for example, methyl (meth)acrylate, ethyl (meth)acrylate, propyl (meth)acrylate, butyl (meth)acrylate and pentyl (meth) acrylate.

More preferably the $(C_1–C_{10})$alkyl (meth)acrylate component comprises at least one $(C_1–C_3)$alkyl methacrylate and at least one $(C_2–C_5)$alkyl acrylate. Most preferably the alkyl (meth)acrylate component comprises methyl methacrylate and butyl acrylate. The amount of the at least one $(C_1–C_3)$alkyl methacrylate in the hair fixative resin is preferably from 5 to 71%, more preferably from 41 to 60%, based on the total monomers used to form the hair fixative resin. The amount of $(C_2–C_5)$alkyl acrylate is preferably from 2 to 67% and more preferably from 10 to 30%, based on the total monomer used to form the acrylic hair fixative resin.

The alkyl group of the hydroxyalkyl (meth)acrylate is preferably a $(C_1–C_5)$alkyl group. For example, the hydroxyalkyl (meth)acrylate is preferably selected from one or more of hydroxyethyl (meth)acrylate, hydroxypropyl (meth) acrylate, hydroxybutyl (meth)acrylate and hydroxypentyl (meth)acrylate. More preferably the hydroxyalkyl (meth) acrylate is selected from one or more of hydroxyethyl methacrylate and hydroxypropyl acrylate.

The $C_3–C_8$ monoethylenically unsaturated monocarboxylic acid monomer is preferably selected from one or more of (meth)acrylic acid and crotonic acid. More preferably, the $C_3–C_8$ monoethylenically unsaturated monocarboxylic acid is methacrylic acid.

The $C_4–C_8$ monoethylenically unsaturated dicarboxylic acid monomer is preferably selected from one or more of itaconic acid, maleic acid and the corresponding anhydrides. Preferably, the $C_4–C_8$ monoethylenically unsaturated dicarboxylic acid monomer is itaconic acid.

The combined amount of the unsaturated monocarboxylic and unsaturated dicarboxylic acid monomer is typically from 3 to 60%, preferably from 12 to 50%, and more preferably from 15 to 25%, based on total weight of the hair fixative resin. At lower levels of combined monocarboxylic and dicarboxylic acid monomer, the degree of stiffness enhancement of hair fixative resin is lessened.

While not wishing to be bound by theory, we believe, in the case of the present invention, that the monomers comprising the acrylic hair fixative resins impart the following properties to the resins: (1) the alkyl acrylate component of the acrylic hair fixative resins plasticizes or reduces the brittleness of the resins, (2) the ($C_1$–$C_3$)alkyl methacrylate component provides hardness to give the resins non-tacky holding properties when applied to the hair as a film, (3) the hydroxyalkyl methacrylate and methacrylic acid components provide shampoo removability without compromising curl retention or tackiness of the resin, and (4) the dicarboxylic acid component strengthens the modulus of the resulting film, and in combination with increased molecular weight, imparts greater stiffness to the hair. The proportions of the monomers comprising the acrylic hair fixative resin are selected to provide for an optimum hydrophilic/hydrophobic balance. This optimum balance provides, in a low-VOC hair styling composition, curl retention under humid conditions, moisture resistance, shampoo removability, and desirable aesthetics to the hair, such as minimal flaking of the hair fixative resin.

The acrylic hair fixative resins preferably have glass transition temperatures ($T_g$) from 35° C. to 140° C., more preferably from greater than 50° C. and up to 100° C., and most preferably from 55° C. to 90° C.

The acrylic hair fixative resins are preferably added to the hair styling composition to provide a total concentration of from 1 to 15%, more preferably from 2 to 10%, and most preferably from 4 to 7%, of the acrylic hair fixative resins, based on the total weight of the hair styling composition.

The acrylic hair fixative resins may be prepared by conventional methods well known to those skilled in the art. The acrylic hair fixative resins are preferably prepared by emulsion polymerization, more preferably by a continuous in-line emulsification process. U.S. Pat. Nos. 3,245,932, 3,453,245 and 4,196,190 may be consulted for further general and specific details on suitable emulsion polymerization methods. Emulsifiers used in the polymer preparation keep the acrylic hair fixative resins suspended in the acrylic hair resin emulsion. Typical emulsifiers used to prepare the acrylic hair fixative resins include, for example, one or more of ($C_8$–$C_{18}$) alcohol sulfates (such as sodium lauryl sulfate and sodium tridecylether sulfate), diester sulfosuccinates, phosphoric acid esters (such as long-chain alkyloxypoly(alkyleneoxide), long-chain alkylaryloxypoly (alkyleneoxide), long-chain alkyl and long-chain alkylaryl mono- and di-esters of phosphoric acid, for example ($C_8$–$C_{18}$)alkylaryloxypoly(alkyleneoxide), ($C_{10}$–$C_{18}$) alkyloxypoly(alkyleneoxide), ($C_{10}$–$C_{18}$)alkyl, and ($C_8$–$C_{18}$) alkylaryl mono- and di-esters of phosphoric acid), alkaryl sulfonates (such as dodecylbenzene sulfonate), alkyl or aryl polyether sulfonates, alkyl or aryl polyether alcohols, ethylene oxide condensates of propylene oxide and propylene glycol adducts. Preferably, the emulsifiers used are anionic type emulsifiers, such as long-chain alkyloxypoly (alkyleneoxide), long-chain alkylaryloxypoly (alkyleneoxide), long-chain alkyl and long-chain alkylaryl mono- and di-esters of phosphoric acid.

The soluble hair fixative resins that are useful in the present embodiment are soluble in the low-VOC hair styling composition "as is" or upon neutralization of some or all of the acid groups contained in the soluble hair fixative resins. The soluble hair fixative resins, if sprayed, preferably have a viscosity less than or equal to $15\times10^{-3}$ pascal•seconds (Pa•sec) (15 centipoise) when dissolved in a pump hair styling composition at a resin concentration of about 5% or less, based on the total weight of the hair styling composition, and less than $25\times10^{-3}$ Pa•sec in an aerosol concentrate.

The acrylic hair fixative resins containing acidic groups, such as carboxylic acid groups, are neutralized by conventional techniques with at least one base to dissolve the resins in the hair styling composition. Bases that will neutralize the soluble hair fixative resins may be selected from one or more amines, alkali or alkaline earth metal hydroxides, and ammonium hydroxide. Suitable amine neutralizers include, for example, 2-amino-2-methyl-1,3-propanediol, 2-amino-2-methyl-1-propanol, N,N-dimethyl-2-amino-2-methyl-1-propanol, monoisopropanolamine, triisopropanolamine, ethanolamine, triethanolamine and morpholine. Suitable alkali or alkaline earth metal hydroxides include, for example, sodium hydroxide and potassium hydroxide. Preferably, the neutralizer is selected from one or more of 2-amino-2-methyl-1,3-propanediol, 2-amino-2-methyl-1-propanol, N,N-dimethyl-2-amino-2-methyl-1-propanol, potassium hydroxide, triethanolamine and triisopropanolamine.

The amount of neutralizer added to the hair styling composition is that amount needed to provide solubility of the soluble hair fixative resins in the hair styling composition. Typically from 5 to 100%, preferably from 10 to 100%, more preferably from 50 to 100%, and most preferably from 75 to 100%, based on molar equivalents, of the acid groups in the hair fixative resins are neutralized.

The low-VOC hair styling compositions may also be blended with one or more other hair fixative resins. Suitable soluble hair fixative resins include, for example, the acrylic hair fixative resins described previously, and other soluble hair resins such as, for example, butyl acrylate/ethyl acrylate/methacrylic acid copolymers, vinyl pyrrolidone/ vinyl acetate copolymers, octylacrylamide/acrylates/ butylaminoethyl-methacrylate copolymers, vinylcaprolactam/vinyl-pyrrolidone/dimethylaminoethyl-methacrylate copolymers, methacryloyl ethylbetaine/ methacrylate copolymers, methacrylic acid/methacrylic ester copolymer, acrylates/hydroxyesters acrylates copolymer and methacrylic acid/acrylic acid ester copolymers. Preferably, the soluble hair fixative resins are the acrylic hair fixative resins described previously.

One or more surfactants may be added to the low-VOC hair styling composition, typically to reduce the surface tension of the composition. When surfactants are present in the hair styling composition, they are preferably present at a concentration of from 0.001 to 1%, based on the total weight of the composition. The surfactants that may be used in the hair styling composition include, for example, anionic, cationic, nonionic and amphoteric surfactants. For example, suitable surfactants include PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate and n-alkyl substituted lactam (such as n-octyl pyrrolidone).

One or more plasticizers may be added to the hair styling composition of the present invention. When plasticizers are present in the hair styling composition, they are preferably present at a concentration of from 0.001 to 1%, based on the total weight of the composition. The plasticizers that may be used in the hair styling composition include, for example, dimethicone copolyol, dimethicone, phenyltrimethicones, trialkylcitrates, and others that are known and typically used in the art.

One or more solvents may be added to the hair styling composition of the present invention. When solvents are added to the hair styling composition they preferably comprise up to 70%, more preferably up to 55%, of the total hair styling composition, based on the total weight of the hair styling composition. Suitable solvents include, for example, $C_2$–$C_6$ organic alcohols (such as ethanol, isopropanol, propyl alcohol) and acetone.

In a low-VOC hair styling composition using an aerosol spray, one or more propellants are used. Preferably the propellants are used at a total concentration of from 10 to 70%, more preferably from 30 to 60%, based on the total weight of the hair styling composition. Suitable propellants include, for example, one or more of n-butane, isobutane, dimethyl ether, difluoroethane, chlorodifluoroethane, chlorodifluoromethane and other chlorofluorocarbons. Preferred propellants are selected from one or more of dimethyl ether, 1,1-difluoroethane, n-butane and isobutane. These propellants are available commercially.

Preservatives that may be used in the low-VOC hair styling composition include, for example, one or more of isothiazolones, iodopropynylbutyl carbamate, benzyl alcohol, imidazolidinylurea and alkyl parabens. A preferred antimicrobial agent is iodopropynylbutylcarbamate (commercially available from Lonza Inc., Fairlawn, N.J.) The preservatives preferably comprise from 0.001 to 1% active ingredient, in the hair fixative resin emulsion.

One or more thickeners may be desirable in a low-VOC hair styling composition that is applied to the hair in the form of a styling gel. Suitable thickeners include, for example, polycarboxylic acid thickeners such as Acrylates/steareth-20 methacrylate copolymer, Acrylates copolymer, or Acrylates $C_{10-30}$ alkyl acrylate crosspolymer; polyethoxylated urethane thickeners and polyamide thickeners. The thickeners, when used, preferably are present at a total concentration of from 0.001 to 5%, based on the total weight of the composition.

Other additives, such as those commonly used by those skilled in the art, may be added to the low-VOC hair styling composition. The other additives used in the hair styling composition will depend upon the type of hair styling composition desired. Other additives include, for example, one or more of fragrances; moisturizers (such as hydrolyzed silk protein and hydrolyzed wheat protein); detangling aids such as panthenol; conditioning agents (U.S. Pat. No. 5,164,177 may be consulted for further general and specific details on suitable conditioning agents); emulsifiers; antistatic aids; extracts; proteins; vitamins; dyes; tints; colorants; UV protectors; and corrosion inhibitors. The other additives typically comprise from 0.005 to 5%, and more preferably from 0.01 to 1%, of the hair styling composition.

Additional other additives, as well as additional surfactants, solvents, other preservatives, and thickeners, that may be suitable in the hair styling composition may be found in the International Cosmetic Ingredients Dictionary, 5th Edition, 1993, published by the Cosmetics Toiletries Fragrances Association (CFTA), Washington D.C.

Examples 1–23 describe preparation of polymer compositions representative of hair fixative resin polymers of the present invention, including comparative compositions (Polymer ID# 2–6, 20, 21 and 23). All ratios, parts and percentages are expressed by weight unless otherwise specified, and all reagents used are of good commercial quality unless otherwise specified. Abbreviations for monomers, emulsifiers and other materials described in the Examples are presented in Table 1. Hair fixative resin monomeric unit composition/emulsifier information is summarized in Table 2.

TABLE 1

| | | |
|---|---|---|
| BA | = | Butyl Acrylate |
| BMA | = | Butyl Methacrylate |
| IBMA | = | Isobutyl Methacrylate |
| TBMA | = | Tertiary-Butyl Methacrylate |
| IBOA | = | Isobornyl Acrylate |
| IBOMA | = | Isobornyl Methacrylate |
| MMA | = | Methyl Methacrylate |
| HEMA | = | Hydroxyethyl Methacrylate |
| DMAM | = | N,N-Dimethylacrylamide |
| MAA | = | Methacrylic Acid |
| IA | = | Itaconic Acid |
| DDM | = | Dodecyl Mercaptan |
| SLS | = | Sodium Lauryl Sulfate |
| PPE-1 | = | Tridecyloxypoly(ethyleneoxide)$_6$ Phosphate (55/45)Mono/Diester |

TABLE 2

| Polymer ID# | Hair Fixative Resin Composition |
|---|---|
| 1 | 25 BA/47 MMA/10 HEMA/13 MAA/5 IA with PPE-1 |
| 1A | 25 BA/47 MMA/10 HEMA/13 MAA/5 IA with SLS |
| 2 (comp) | 25 BA/47 MMA/10 HEMA/18 MAA with SLS |
| 3 (comp) | 25 IBMA/47 MMA/10 HEMA/18 MAA with SLS |
| 4 (comp) | 25 TBMA/47 MMA/10 HEMA/18 MAA with SLS |
| 5 (comp) | 10 IBOA/15 BA/47 MMA/10 HEMA/18 MAA with SLS |
| 6 (comp) | 10 IBOMA/15 BA/47 MMA/10 HEMA/18 MAA with SLS |
| 7 | 25 BA/52 MMA/10 HEMA/8 MAA/5 IA with PPE-1 |
| 8 | 25 BMA/47 MMA/10 HEMA/13 MAA/5 IA with SLS |
| 9 | 25 BMA/47 MMA/5 HEMA/5 DMAM/13 MAA/5 IA with SLS |
| 9A | 30 BMA/47 MMA/10 HEMA/8 MAA/5 IA with SLS |
| 10 | 25 BMA/42 MMA/10 HEMA/5 DMAM/13 MAA/5 IA with SLS |
| 11 | 23 BA/2 IBOMA/47 MMA/10 HEMA/13 MAA/5 IA with PPE-1 |
| 12 | 21 BA/4 IBOMA/47 MMA/10 HEMA/13 MAA/5 IA with PPE-1 |
| 13 | 18 BA/7 IBOMA/47 MMA/10 HEMA/13 MAA/5 IA with PPE-1 |
| 14 | 25 BA/57 MMA/13 MAA/5 IA with PPE-1 |
| 15 | 25 BA/55 MMA/2 HEMA/13 MAA/5 IA with PPE-1 |
| 16 | 25 BA/47 MMA/10 HEMA/11 MAA/7 IA with PPE-1 |
| 17 | 25 BA/47 MMA/10 HEMA/8 MAA/10 IA with PPE-1 |
| 18 | 23 BA/2 IBOA/47 MMA/10 HEMA/13 MAA/5 IA with PPE-1 |
| 19 | 21 BA/4 IBOA/47 MMA/10 HEMA/13 MAA/5 IA with PPE-1 |
| 20 (comp) | 21 BA/4 IBOA/47 MMA/10 HEMA/18 MAA with SLS |
| 21 (comp) | 18 BA/7 IBOA/47 MMA/10 HEMA/18 MAA with SLS |
| 22 | 21 BA/4 IBOMA/47 MMA/10 HEMA/13 MAA/5 IA with SLS |
| 23 (comp) | 21 BA/4 IBOMA/47 MMA/10 HEMA/18 MAA with SLS |

The hair styling compositions for testing were prepared as follows: 5% hair resin polymer (% active solids), 50–100% neutralized with 2-amino-2-methyl-1-propanol, 55% ethanol (100%), balance made up with water. Compositions in Table 3 were evaluated at 55% VOC, 50% neutralization, unless indicated otherwise. A non-dicarboxylic acid-containing polymer (Polymer #2) was used as a control for determining stiffness enhancement of the acrylic hair fixative resins of the present invention. The SEF ratio (described below) is the ratio of the stiffness of the hair styling composition containing a hair fixative resin relative to that of the hair styling composition containing Polymer #2.

The hair fixative performance data reported in Table 3 are based on several different properties, primarily the hair stiffness enhancement of the treated hair; drawn film clarity/uniformity and high humidity curl retention properties were satisfactory unless indicated otherwise. The hair styling compositions of the present invention contain hair fixative resins that provide a stiff-feel ("stiffness enhancement") to the hair, as measured by curl compression of the treated hair relative to hair treated with prior art hair fixative resins (that is, those hair fixative resins that do not contain dicarboxylic acid monomer). The "stiffness enhancement factor" (or SEF) is a relative measure of this improvement. Preferably, hair styling compositions of the present invention provide an SEF of at least 1.2, more preferably at least 1.5, and most preferably at least 1.7, based on curl compression of hair samples treated with the hair fixative resin. Example 24 describes these tests in detail.

Data in Table 3 show stiffness enhancement for hair fixative resins having weight average molecular weights ranging from 48,000 to 153,000. Hair fixative resins containing no dicarboxylic acid monomer (#2, 3, 4, 5, 6, 20, 21 and 23) are deficient in stiffness enhancement, film clarity or curl retention properties. Levels of neutralization of the carboxyl groups in the hair fixative at 75% and 100% (#1, 1A, 8 and 12–15) provided satisfactory properties in addition to the 50% neutralization level. Various levels of the hydroxyalkyl (meth)acrylate monomer component (from zero to 10%) provide satisfactory properties (#1, 9, 14 and 15). Various levels of the dicarboxylic acid monomer component (from 5 to 10%) provide satisfactory properties (#15, 16 and 17). Additional hair fixative resins in Table 3 represent various combinations of different ($C_1$–$C_{10}$)alkyl (meth)acrylate monomer components (BA, IBOA, IBOMA, MMA and BMA).

TABLE 3

| Polymer Composition | SEF Ratio | Drawn Film Clarity | $M_w{}^a$ |
|---|---|---|---|
| 1 | 1.31 | + | 48K |
| 1 | 1.28 | + | 71K |
| 1 | 1.36 | + | 104K |
| 1 | 1.55 | + | 153K |
| 1 | 1.57 | + | 78K |
| 1[c] | 1.45 | + | 78K |
| 1A | 1.36 | + | |
| 1A[b] | 1.91 | + | |
| 1A | 1.64 | + | 116K |
| 2 (comp) | [1.0] | + | 50K |
| 3 (comp) | 1.12 | − | |
| 4 (comp) | 1.05 | − | |
| 5 (comp) | 1.47 | −[d] | |
| 6 (comp) | 1.08 | − | |
| 7 | 1.0 | + | 62K |
| 8 | 1.52 | + | |
| 8[b] | 1.19 | + | |
| 8[c] | 1.27 | + | |
| 9 | 2.22 | + | 63K |
| 9A | 1.0 | + | |
| 10 | 1.80 | + | |
| 11 | 1.72 | + | |
| 12 | 1.69 | + | |
| 12[b] | 1.41 | + | |
| 13[b] | 1.33 | + | |
| 14[c] | 1.71 | + | |
| 15[b] | 1.56 | + | |
| 16 | 1.52 | + | |
| 17 | 1.51 | + | |
| 18 | 1.83 | + | |
| 19 | 1.28 | + | |
| 20 (comp) | 1.31 | − | |
| 21 (comp) | — | − | |
| 22 | 2.00 | + | |
| 23 (comp) | 1.37 | − | |

[a] is approximately 50K (50,000) unless indicated otherwise.
[b] hair fixative resin 75% neutralized.
[c] hair fixative resin 100% neutralized.
[d] poor high humidity curl retention.

EXAMPLE 1

To a three liter, four-neck round bottom flask equipped with overhead stirrer, condenser, nitrogen adapter and a thermocouple was added 43.5 grams (g) itaconic acid (IA) powder, 255.0 g deionized water and 8.5 g of 25% (in water) mixed phosphate ester emulsifier as ammonium salt (55/45 weight ratio mixture of mono-tridecyloxypoly (ethyleneoxide) and di-tridecyloxypoly(ethyleneoxide) esters of phosphoric acid having an average of 6 ethyleneoxide units per group [PPE-1 in Table 1]; available as Rhodafac RS-610A from Rhône-Poulenc; Rhodafac is a trademark of Rhône-Poulenc Inc.). With the nitrogen turned on, the reactor and contents were heated to 83° C. and an initiator solution of 2.2 g ammonium persulfate and 17.5 g deionized water was added with stirring. After the initiator solution was charged, 50 g of monomer emulsion, from a monomer emulsion containing 388 g deionized water, 12.75 g mixed phosphate ester emulsifier, 408.9 g methylmethacrylate (MMA), 217.5 g butylacrylate (BA), 87 g hydroxyethylmethacrylate (HEMA), 113.1 g methacrylic acid (MAA) and 11.0 g n-dodecyl mercaptan (DDM), was charged to the reactor. The remaining monomer emulsion feed was then fed over 120 minutes while maintaining a temperature of 83° C. A cofeed initiator solution containing 0.73 g ammonium persulfate and 79.0 g deionized water was gradually added simultaneously with the monomer emulsion feed over 120 minutes.

After the monomer emulsion and initiator feeds were complete, the reaction mixture was "chased" with a ferrous sulfate, t-butyl hydroperoxide, ammonium persulfate and d-isoascorbic acid combination to reduce residual monomer levels. The reaction mixture was then cooled to room temperature and filtered. The composition of the resulting polymer was 47 MMA/25 BA/10 HEMA/13 MAA/5 IA. The amount of PPE-1 emulsifier was 0.6%, based on total monomer weight.

EXAMPLE 1A

An emulsion polymer composition was again prepared according to the procedure in Example 1 except for the surfactant employed and its total amount based on monomer. Sodium lauryl sulfate (28% aqueous solution) was charged at 8.5 g as part of initial reactor charge and 4.25 g as part of the monomer emulsion.

EXAMPLES 2–23

Polymer compositions 2–23 were prepared similarly to Examples 1 and 1A and are representative of hair fixative resin polymers of the present invention, including comparative compositions. Compositional information is presented in Table 2.

EXAMPLE 24

Hair Formulation Performance Tests
Hair Stiffness

Pretreatment: The hair tresses (European brown virgin hair, obtained from International Hair Importers and Products, White Plains, N.Y.) prior to curling were on the average 6 inches long and weighed 3.5±0.1 grams. They were washed in mild shampoo before using and curled wet onto a 22 millimeter (mm)×70 mm curler and held in place with a bobby pin. The curled tresses were allowed to dry on the lab bench overnight.

Stiffness measurement: The curled tresses were uniformly sprayed twice in the front and twice on the back from a distance of 20.3 centimeters (cm) (8 inches) with hair spray formulations containing hair fixative resins as described in Table 2. They were placed on the lab bench to dry for 1 hour.

The curler was removed carefully without uncurling the tress. The curled tress was placed in the miniature tensile tester, model MTT160 instrument (Dia-Stron Limited, Unit 9 Focus 303 Business Centre, Andover, Hampshire SP10 5NY UK, or 390 Reed Road, Broomall, Pa. 19008, USA) and the work measured to compress the curl to 40% of its initial diameter was measured. The spray device delivered 140 μL (microliters) of formulation to the hair with each pump compression. The spray device product was 'Euromist II' and was manufactured by SequistPerfect, Cary, Ill. For untreated hair tresses, the curl compression work was approximately 4.5 millijoules (mjoule); for hair tresses treated with Polymer #2, the curl compression work typically ranged from 10 to 15 mjoule; for hair tresses treated with polymers useful in the present invention, the curl compression work typically ranged from 15 to 25 mjoule.

High Humidity Curl Retention

The amount of hair fixative formulation sprayed on the hair was the same as described above for the stiffness measurements. The following procedure was used to evaluate each test hair styling composition:

Each test hair styling composition was sprayed on a 2 gram swatch of European brown virgin hair having a length of 16.5 cm (6.5 inches), pre-glued at root end, and supplied by International Hair Importers, White Plains, N.Y. Each hair swatch was washed with a dilute solution of "Suave" shampoo (trademark of Helene Curtis), followed by rinsing with ambient temperature deionized water. Each test hair styling composition was sprayed onto the hair swatch using a Euromist II spray valve; the spray valve dispensed about 140 μL per pump stroke.

Percent curl retention of each test hair styling composition was evaluated by rolling the hair swatch, previously described, in a curler having a diameter of about 3 cm. The hair was then sprayed with about 700 μL of the test hair styling composition. The hair was allowed to completely dry. After drying, the curler was removed from the hair and the hair was placed in a chamber having 95 percent relative humidity for 8 hours. The percent curl retention was measured by measuring the length of the hair initially after curling ($L_i$), the length of the hair after exposure to humidity ($L_r$), and the length of the hair fully extended, before curling ($L_e$). The following equation (Formula I) was used to calculate percent curl retention. Satisfactory curl retention values are greater than 70%, preferably greater than 80%, and more preferably greater than 85%.

$$\% \text{ Curl Retention} = \frac{(L_e - L_r) \times 100}{(L_e - L_i)} \quad \text{Formula I}$$

Molecular Weight Effects

The acrylic hair fixative resins useful in the present invention were evaluated for the effect of resin weight average molecular weight ($M_w$) on the performance of low-VOC hair styling compositions. The acrylic hair fixative resins preferably have a $M_w$ from 40,000 to 200,000, more preferably from 50,000 to 150,000, and most preferably from 75,000 to 130,000, as measured by gel permeation chromatography (GPC) using a 100,000 $M_w$ methyl methacrylate polymer as the standard. Hair fixative resins having $M_w$ below 40,000 do not provide the stiffness on hair required by the present invention; those resins having $M_w$ above 200,000 do not allow for satisfactory sprayability of hair styling composition due to high viscosity.

Film Clarity

A hair fixative formulation was prepared by mixing the following components: 5% active polymer, 55% ethanol (100%), 0.7% 2-amino-2-methyl-1-propanol and 39% deionized water. Approximately 2 milliliters (mL) of the formulation was placed on a clean glass plate and a film was drawn across the plate with a 0.004 mil (0.000004 inch= 0.0000102 centimeter) thickness draw down block. The film was observed for opacity while drying and after it had dried: if the film remained clear throughout, it passed the test (+) and if there was any opacity or cracking while the film was drying or after it had dried, the film failed the test (−).

We claim:

1. An aqueous hair styling composition comprising:
   (a) from 1 to 15 weight percent of at least one acrylic hair fixative resin, wherein the acrylic hair fixative resin is a polymer comprising as polymerized units: (i) 5 to 95 weight percent of at least one ($C_1$–$C_{10}$)alkyl (meth) acrylate, (ii) from 2 to 26 weight percent of least one hydroxyalkyl (meth)acrylate, (iii) from zero to 50 weight percent from of at least one $C_3$–$C_8$ monoethylenically unsaturated monocarboxylic acid monomer and (iv) from 2 to 10 weight percent of at least one $C_4$–$C_8$ monoethylenically unsaturated dicarboxylic acid monomer, based on total weight of the acrylic hair fixative resin; and
   (b) at least one neutralizer.

2. The composition of claim 1 wherein:
   (i) the ($C_1$–$C_{10}$)alkyl (meth)acrylate is from 2 to 67 weight percent of at least one ($C_2$–$C_5$)alkyl acrylate and from 5 to 71 weight percent of methyl methacrylate;
   (ii) the hydroxyalkyl (meth)acrylate is hydroxyethyl methacrylate;
   (iii) the $C_3$–$C_8$ monoethylenically unsaturated monocarboxylic acid monomer is from 2 to 30 weight percent of methacrylic acid; and
   (iv) the $C_4$–$C_8$ monoethylenically unsaturated dicarboxylic acid monomer is itaconic acid.

3. The composition of claim 1 wherein the neutralizer is selected from one or more of 2-amino-2-methyl-1,3-propanediol, 2-amino-2-methyl-1-propanol, N,N-dimethyl-2-amino-2-methyl-1-propanol, potassium hydroxide, triethanolamine and triisopropanolamine.

4. The composition of claim 1 further comprising volatile organic compounds in a concentration up to 98 weight percent, based on total weight of the aqueous hair styling composition.

5. The composition of claim 4 wherein the volatile organic compounds are selected from one or more of ethanol, isopropanol, n-propanol, dimethoxymethane, dimethylether and $C_1$–$C_{12}$ straight or branched chain hydrocarbons.

6. The composition of claim 4 wherein the volatile organic compounds concentration is 80 weight percent or less.

7. The composition of claim 1 further comprising a propellant selected from one or more of dimethyl ether, 1,1-difluoroethane, n-butane and isobutane.

8. The composition of claim 1 wherein the composition has a stiffness enhancement factor of at least 1.2, wherein the stiffness enhancement factor is the the ratio of the stiffness of the hair styling composition containing the hair fixative resin of claim 1 relative to that of a hair styling composition containing a hair fixative resin that does not contain dicarboxylic acid monomer.

9. The composition of claim 1 wherein the polymer has a glass transition temperature from 35° C. to 140° C.

10. The composition of claim 1 wherein the polymer has a weight average molecular weight from 40,000 to 200,000.

11. The composition of claim 1 wherein 10 to 100 percent of the polymer has been neutralized, based on molar equivalents of acid groups in the hair fixative resin.

12. The composition of claim 1 wherein the $C_3$–$C_8$ monoethylenically unsaturated monocarboxylic acid monomer and the $C_4$–$C_8$ monoethylenically unsaturated dicarboxylic acid monomer are present in a combined amount of from 3 to 60 weight percent, based on total weight of the acrylic hair fixative resin.

13. A method for increasing the stiffness on hair of aqueous hair styling compositions comprising introducing from 1 to 15 weight percent of an acrylic hair fixative resin, based on total weight of the aqueous hair styling composition, into a hair styling composition, wherein:
   (a) the acrylic hair fixative resin is a polymer comprising as polymerized units:
      (i) 5 to 95 weight percent of at least one $(C_1-C_{10})$alkyl (meth)acrylate,
      (ii) from 2 to 26 weight percent of least one hydroxyalkyl (meth)acrylate,
      (iii) from zero to 50 weight percent from of at least one $C_3-C_8$ monoethylenically unsaturated monocarboxylic acid monomer, and
      (iv) from 2 to 10 weight percent of at least one $C_4-C_8$ monoethylenically unsaturated dicarboxylic acid monomer, based on total weight of the acrylic hair fixative resin; and
   (b) the hair styling composition comprises at least one neutralizer.

14. The method of claim 13 wherein:
   (i) the $(C_1-C_{10})$alkyl (meth)acrylate is from 2 to 67 weight percent of at least one $(C_2-C_5)$alkyl acrylate and from 5 to 71 weight percent of methyl methacrylate;
   (ii) the hydroxyalkyl (meth)acrylate is hydroxyethyl methacrylate;
   (iii) the $C_3-C_8$ monoethylenically unsaturated monocarboxylic acid monomer is from 2 to 30 weight percent of methacrylic acid; and
   (iv) the $C_4-C_8$ monoethylenically unsaturated dicarboxylic acid monomer is itaconic acid.

15. The composition of claim 1 wherein the $C_3-C_8$ monoethylenically unsaturated monocarboxylic acid monomer is from 12 to 26 weight percent, based on total weight of the acrylic hair fixative resin.

16. The composition of claim 1 wherein the polymer has a glass transition temperature from greater than 50° C. and up to 100° C.

17. The composition of claim 12 wherein the combined amount of unsaturated monocarboxylic acid monomer and unsaturated dicarboxylic acid monomer is from 12 to 50 weight percent, based on total weight of the acrylic hair fixative resin.

18. The composition of claim 12 wherein the combined amount of unsaturated monocarboxylic acid monomer and unsaturated dicarboxylic acid monomer is from 15 to 25 weight percent, based on total weight of the acrylic hair fixative resin.

* * * * *